United States Patent [19]

Nowinski

[11] Patent Number: 5,068,178

[45] Date of Patent: Nov. 26, 1991

[54] METHOD OF ENHANCING DIRECT IMMUNOFLUORESCENCE STAINING OF CELLS

[75] Inventor: Robert C. Nowinski, Bothell, Wash.

[73] Assignee: Genetic Systems Corporation, Redmond, Wash.

[21] Appl. No.: 517,953

[22] Filed: Apr. 27, 1990

Related U.S. Application Data

[63] Continuation of Ser. No. 282,911, Dec. 6, 1988, abandoned, which is a continuation of Ser. No. 934,165, Nov. 21, 1986, abandoned, which is a continuation of Ser. No. 629,094, Jul. 9, 1984, abandoned.

[51] Int. Cl.$^5$ ........................................... G01N 33/577
[52] U.S. Cl. ..................................... 435/7.2; 435/7.24; 435/7.7; 435/7.71; 435/7.8; 435/7.9; 435/34; 436/519; 436/548; 436/800; 436/801; 436/824; 436/828
[58] Field of Search ..................... 435/7, 29, 34, 7.2, 435/7.24, 7.7, 7.71, 7.8, 7.9; 436/519, 548, 800, 801, 824, 828

[56] References Cited

U.S. PATENT DOCUMENTS 4,361,550 11/1982 Kung et al. .......................... 424/85
4,381,295  4/1983 Kung et al. .......................... 424/85

OTHER PUBLICATIONS

F. M. Kourilsky et al., *Europ. Jour. Immunol*, 2, 249, 257, 1972.
J. J. Langone, *Meth Enzymol*, 70, 372, 1980.
R. L. Matthews et al., *Jour. Immunol. Meth.*, 28, 219-232, 1979.
C. Neauport-Sautes et al., *Jour. Exper. Med.*, 137, 511-526, 1973.
E. Soini, *Clin. Chem.*, 25, 353-361, 1979.
Taylor et al., *Nature New Biology*, 233, 225-229, 1971.
Reinharz, E. L. & S. F. Schlossman, *Cell* 19: 821, 1980.
Cosimi et al., *New England J. Medicine* 306: 308, 1981.
Bach et al., *Ann Immunol.* 133: 131, 1982.
Johnson et al., *Handbook of Experimental Immunology*, D. M. Weir, Ed., Oxford: Blackwell Publications, 1979 (pp. 15.1-15.18).

*Primary Examiner*—David Saunders
*Attorney, Agent, or Firm*—Townsend and Townsend

[57] ABSTRACT

A method of identifying and enumerating specific cell types in a heterogeneous population of cells by enhancing the specific staining of desired cells, comprising contacting a sample from the heterogeneous population of cells with a labeled primary antibody which recognizes and binds to a desired cell surface antigen and an unlabeled cross-linking agent which recognizes and binds to the primary antibody is disclosed.

16 Claims, No Drawings

METHOD OF ENHANCING DIRECT IMMUNOFLUORESCENCE STAINING OF CELLS

CROSS REFERENCE TO RELATED APPLICATIONS

This application is a continuation of application Ser. No. 282,911, filed Dec. 6, 1988 and now abandoned, which is a continuation of application Ser. No. 934,165, filed Nov. 21, 1986 and now abandoned, which is a continuation of application Ser. No. 629,094, filed July 9, 1984 and now abandoned.

DESCRIPTION

1. Technical Field

This invention relates to immunochemical methods for identifying and enumerating specific cell types in a heterogeneous population, and more particularly, to a method for enhancement of the sensitivity of immunofluorescence identification of cells.

2. Background Art

There are numerous examples in the literature of cell surface antigens which define specific cell types, For example, it is possible to distinguish at least two subsets of human T-lymphocytes in peripheral blood based on their surface antigens [Reinherz and Schlossman, Cell, volume 19, 82 (1980); Reinherz et al., J. Immunol., volume 23, 1312 (1979)]. T-lymphocytes belonging to the $T_{S/C}$ subclass are characterized by an antigen of molecular weight 32,000 Daltons (determined by electrophoresis in sodium dodecyl sulfate-containing polyacrylamide gels). T-lymphocytes belonging to the $T_{H/I}$ subclass, on the other hand, are characterized by an antigen of molecular weight 55,000 Daltons.

Both polyclonal and monoclonal antibodies have been made which recognize the $T_{S/C}$ or the $T_{H/I}$ antigens. U.S. Pat. No. 4,361,550, issued November 30, 1982 to Kung et al., describes the production of monoclonal antibodies to the $T_{S/C}$ antigen, which they call "OKT8". U.S. Pat. No. 4,381,295, issued Apr. 26, 1983 to Kung et al., describes the production of monoclonal antibodies to the $T_{H/I}$ antigen, which they call "OKT4".

The above-cited antibodies can be labeled directly or indirectly and may be used to identify and enumerate the $T_{S/C}$ and $T_{H/I}$ subsets in peripheral blood. Such determinations are thought to be useful for evaluating certain immune disorders. [Cosimi et al., New Engl. J. Med., volume 306, 308 (1981); Kornfeld et al., N. Engl. J. Med., volume 307, 799 (1982); Bach et al., Ann. Immunol., volume 133, 131 (1982).]

Immunofluorescence staining methods are widely used in research and diagnostics to demonstrate the presence of specific antigenic determinants on cells or tissues and to quantify the numbers of cells bearing particular determinants in a heterogeneous population.

Immunofluorescence staining methods can be divided into two categories, direct and indirect methods. In the direct staining method, a fluorophore is conjugated to an antibody (hereinafter called "the primary antibody") which is capable of binding directly to the cell surface antigen of interest. In the indirect staining method, the primary antibody is not fluorescently labeled; its binding is visualized instead by the binding of a fluorescently labeled second-step antibody, which second-step antibody is capable of binding to the primary antibody. Typically, the second-step antibody is an anti-immunoglobulin antibody. TM Indirect immunofluorescence is advantageous in that it is more sensitive than direct immunofluorescence because for each molecule of the primary antibody which is bound, several molecules of the labeled second-step antibody can bind. This leads to a geometric increase in the amount of cell-associated fluorescence. However, it is well known in the art that indirect immunofluorescence is more prone than direct immunofluorescence to nonspecific staining, that is, staining which is not due to the specific antigen-antibody interaction of interest. [Johnson et al, in Handbook of Experimental Immunology, D. M. Weir, ed., Oxford: Blackwell Publications (1979); Mishell et al., ed., Selected Methods in Cellular Immunology, San Francisco: W. H. Freeman (1980).]

In order to reduce the amount of nonspecific staining, it is necessary to exhaustively purify the second-step antibody. Such purification is laborious and time-consuming, and it is often impossible to lower the background staining to an acceptable level even after purification. Consequently, there is a need in the art for an immunochemical method of identifying cells which is both sensitive and specific. The present invention fulfills this need, and further provides other related advantages.

DISCLOSURE OF INVENTION

The present invention discloses a method for identifying and enumerating specific cell types in a heterogeneous population of cells which enhances the specific staining of desired cells. Essential features of the method include: (a) contacting a heterogeneous population of cells with a primary labeled antibody which recognizes and binds to a desired cell surface antigen characteristic of a given cell type; (b) washing the population to remove unbound labeled primary antibody; (c) contacting the population with an unlabeled cross-linking agent which recognizes and binds to the primary antibody; and (d) detecting the cells which have been labeled by binding to the primary antibody.

The unlabeled cross-linking agent is typically an antibody to the primary antibody or an antibody binding protein such as protein A. It is believed to cross-link the primary antibody-antigen complex in the plane of the cell membrane, thereby concentrating the label into discrete areas on the cell surface so that a more accurate and precise count of the stained cells is possible. However, since the cross-linking agent is not itself labeled, nonspecific binding is not detected.

BEST MODE FOR CARRYING OUT THE INVENTION

The identification and enumeration of specific cell types in a heterogeneous population of cells, such as blood, is becoming increasingly important in medical diagnostics. Of particular interest is the enumeration of various sets and subsets of lymphocytes in human blood.

With the advent of monoclonal antibody technology [Kohler and Milstein, Nature, volume 256, 495 (1974)], it became possible to produce exquisitely specific antibodies with which to probe the cell surface. Several such antibodies have been developed which recognize antigenic determinants unique to specific subsets of human T-lymphocytes which had previously been distinguished on a functional basis. These antibodies and the methods by which they are produced are described in U.S. Pat. Nos. 4,361,550 and 4,381,295, which are herein incorporated by reference.

Because of their defined specificity, monoclonal antibodies are generally preferred to polyclonal antibodies as the primary antibodies in the method of this invention. However, the latter may be used if care is taken to remove unwanted specificities, as, for example, by absorption.

In general, it is necessary to at least partially purify the primary antibody before labeling. Methods of purification are well known [Mishell et al., ed., Selected Methods in Cellular Immunology, San Francisco: W. H. Freeman and Co. (1980)] and can include ammonium sulfate fractionation, ion exchange chromatography, gel filtration chromatography, affinity chromatography, or some combination thereof.

A variety of labeling substances are described in the patent and non-patent literature. These include fluorophores, radioisotopes, enzymes, dyes, enzyme cofactors, enzyme inhibitors, luminescent materials, ferritin, colloidal gold, etc. [see, for example, Langone et al., eds., Methods in Enzymology, volume 70, N.Y.: Academic Press (1980)]. Because of the ready availability of fluorescence microscopes in the laboratory, the preferred labeling substance in the instant invention is a fluorophore, typically fluorescein, rhodamine, phycoerythrin, or phycocyanin.

Methods of labeling antibodies with fluorophores are known in the art [Weir, ed., Handbook of Experimental Immunology, Oxford: Blackwell Publications (1979)]. Typically, antibody (as an IgG fraction) is incubated with fluorescein isothiocyanate (FITC) at an approximate ratio of 45 ug FITC per mg of antibody protein for about one hour at 37° C. Labeled antibody is separated from free label by gel filtration, for example, on Sephadex G-25.

Labeling with phycoerythrin (PE) or phycocyanin (PC) is typically accomplished as described by Oi et al. [J. Cell Biol., volume 93, 981 (1982); European patent application 76,695, filed October 5, 1982]. Briefly, thioalted phycoerythrin is coupled to IgG via a heterobifunctional cross-linking agent, such as N-succinimidyl 3-(2-pyridylthio)-propionate (SPDP).

The cross-linking agent is typically an antibody or a non-immunoglobulin antibody-binding protein. If it is an antibody it is typically an anti-immunoglobulin antibody. For example, if the primary antibody is a mouse monoclonal antibody, a rabbit or goat anti-mouse immunoglobulin antibody can be used as the cross-linking agent. It is also possible, however, to use an anti-label antibody as the second-step agent, provided that the signal-emitting properties of the label are not diminished by antibody binding.

The cross-linking antibody can be a monoclonal antibody or a polyclonal antibody. Since the second-step antibody is unlabeled, it is not necessary that it be completely specific for the primary antibody. Generally, it is preferred to use the cross-linking antibody as an immunoglobulin (Ig) or IgG fraction of serum. The cross-linking antibody can also be affinity purified, if desired.

The cross-linking agent can also be an antibodybinding protein, such as protein A from *Staphylococcus aureus*. Similar non-immunoglobulin antibody-binding proteins can be isolated from other bacterial species, e.g., Streptococcus, as well. If a non-immunoglobulin antibodybinding protein is used as the unlabeled cross-linking agent, it is important in choosing the primary antibody that it be of a subclass capable of binding to the antibody-binding protein. For example, Staphylococcal protein A binds to mouse IgG of the $\lambda 2a$ $\lambda 2b$, and $\lambda 3$ subclasses, but not to mouse IgG of the $\lambda 1$ subclass.

The cell population to be assayed can be prepared in a variety of ways, depending on the source of the sample and the cell type of interest. When the sample is peripheral blood and the cells of interest are T-cells, whole blood is typically layered onto a separation medium, such as Ficoll-Hypaque, and the lymphocytes are recovered from the interface after density gradient centrifugation. The cells so obtained are washed in a suitable buffer and resuspended to a desired concentration. Viability can be determined, if desired, by staining with a vital dye. In addition to subsets of T-cells, there are numerous other cell types whose presence and number can be of interest. For example, one might wish to detect tumor cells in a patien's circulation, or cells of host origin in the circulation of a transplant recipient. The possibilities are limited only by the availability of the appropriate monoclonal antibodies.

The assay of this invention is generally carried out in the following manner. Isolated mononuclear cells are suspended in phosphate buffered saline, pH 7.4, (PBS) to a concentration of approximately $1 \times 10^7$ viable cells/ml. 10 uL of labeled primary antibody is added to 100 uL of the cell suspension and the mixture is incubated briefly 5–30 minutes) on ice. The cells are washed with PBS and pelleted by centrifugation. The pellet is resuspended in 100 uL of PBS containing approximately 1 ug/mL crosslinking agent. After another brief incubation, the cells are again washed and the pellet resuspended in a suitable mounting medium. One drop (about 10 uL) of the suspension is transferred to a clean microscope slide. Approximately 200 cells (stained and unstained) are counted on a fluorescence microscope equipped with standard fluorescein filters ($\lambda$excitation = 490 nm; $\lambda$emission = 520 nm) and a 63× oil immersion lens.

In the absence of the cross-linking agent, the fluorescence staining pattern is observed to be dull and diffuse. Addition of the unlabeled cross-linking agent causes the staining pattern to become much brighter and sharper, enabling a more accurate and precise count of the number of positively stained cells.

The exact mechanism by which the cross-linking agent increases the sensitivity of the assay is not known. It is thought that binding of the cross-linking agent induces a redistribution of the primary antibody-antigen complex in the plane of the cell membrane by cross-linking the primary antibody. It is known in the literature that membrane proteins are mobile in the plane of the membrane and that they can be caused to patch or cap by the addition of antibodies which cross-link them [see for example, Reinherz et al., Cell, volume 30, 735 (1982].

The example presented hereinafter is presented by way of illustration and not by way of limitation.

EXAMPLE

Identification and Enumeration of Helper T-cells ($T_{H/I}$)

A fluorescein-labeled mouse monoclonal antibody to the $T_{H/I}$ subset of human T-lymphocytes was obtained from Ortho Diagnostic Systems (Westwood, Mass.). This antibody is designated FITC-OKT4 and its preparation and characterization is the subject of U.S. Pat. No. 4,381,295. The cell line which produces this antibody has been deposited with the ATCC and given the accession number CRL 8002.

Affinity-purified goat anti-mouse IgG (GAM) was obtained from Tago (Burlingame, CA) and diluted 1:160 in normal saline containing 1 mg/mL bovine serum albumin (BSA) and 0.1% (w/v) sodium azide. This reagent is referred to as unlabeled GAM. Fluorescein-conjugated GAM (FITC-GAM) was obtained from Ortho Diagnostic Systems and diluted 1:20 before use.

Blood samples were collected in heparin-containing tubes by venipuncture. Lymphocytes were isolated within 2 hours of collection by density gradient centrifugation on Lymphocyte Separation Medium (9.4% sodium diatrizoate/6.2% Ficoll, having a density of 1.077 g/mL at 20° C.; available from Litton Bionetics, Kensington, Md.).

Whole blood (4mL) was diluted with an equal volume of PBS and mixed by inversion. 4 mL of diluted blood was carefully layered onto 4 mL of room-temperature lymphocyte separation medium (LSM). Each sample was centrifuged at 22° C. for 40 minutes at 1500 rpm. The plasma layer was aspirated and discarded, and the mononuclear cell layer (which forms at the plasma/LSM interface) was transferred to a clean tube using a Pasteur pipette. The cells were washed once with approximately 15 mL of PBS, resuspended in 0.5 ml of PBS, and counted on a hemacytometer. The cell concentration was adjusted to $1 \times 10^7$ viable cells/mL with PBS. Cell viability was determined to be at least 70% by staining with 0.01% (w/v) trypan blue in PBS.

100 uL of the cell suspension prepared above was mixed with 10 uL of fluorescein-labeled anti-$T_{H/I}$ reagent or 10 uL of PBS (control) and the mixture incubated 30 minutes on ice. 2 mL of PBS was added and the cells were pelleted by centrifugation at 400 × g for 10 minutes.

The supernatant was withdrawn and the pellet was resuspended in 100 uL of either unlabeled GAM or PBS. The control (no primary antibody) was resuspended in FITC-GAM to assess the amount of nonspecific staining. The cells were incubated for 30 minutes on ice and washed twice with PBS. After the second wash, the cell pellets were resuspended in two drops of 30% (v/v) glycerol in PBS and 10 uL of each suspension transferred to a clean microscope slide. The slides were examined under a fluorescence microscope using a 63× oil immersion lens and standard fluorescein filters.

$T_{H/I}$ cells stained with FITC-OKT4 and unlabeled GAM showed a clearly distinguished rim-like pattern of speckled, apple-green fluorescence. When the labeled cell pellet was resuspended in PBS alone (without GAM), the fluorescence was uniformly dull, making it difficult to accurately count the labeled cells. When a labeled, $T_{H/I}$-positive cells stained brightly, but in some experiments, as many as 16% of the cells in the control (which lacked primary antibody) stained nonspecifically.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method of identifying and enumerating a specific cell type in a heterogenous population of cells which enhances the specific staining of desired cells, comprising:
    (a) contacting a sample from said heterogeneous population of cells with a primary labeled antibody which recognizes and binds to a desired cell surface antigen, the presence of said antigen being characteristic of said specific cell type;
    (b) washing said sample to remove unbound labeled primary antibody;
    (c) contacting said sample with an unlabeled cross-linking agent which recognizes and binds to said primary antibody within the plane of the cellular membrane;
    (d) detecting the cells which have been lebeled by binding to said primary antibody; and
    (e) relating the detection of step (d) to the identification and enumeration of the specific cell type;
    wherein steps (a), (b) and (c) are carried out at the temperature of an ice bath and there is no incubation at 37° C. between steps (c) and (d).

2. The method of claim 1 wherein the primary antibody is a monoclonal or polyclonal antibody.

3. The method of claim 1 wherein the substance used to label the primary antibody is one selected from the group consisting of fluorophores, radioisotopes, enzymes, dyes, enzyme cofactors, enzyme inhibitors, luminescent materials, ferritin, and colloidal gold.

4. The method of claim 1 wherein the substance used to label the primary antibody is a fluorophore.

5. The method of claim 3 wherein the fluorophore is one selected from the group consisting of fluorescein, rhodamine, phycoerythrin, and phycocyanin.

6. The method of claim 1 wherein the second, unlabeled cross-linking agent is a monoclonal or polyclonal antibody.

7. The method of claim 1 wherein the unlabeled cross-linking agent is a non-immunoglobulin antibody-binding protein.

8. The method of claim 7 wherein the non-immunoglobulin antibody-binding protein is protein A.

9. The method of claim 6 wherein the unlabeled antibody is an anti-immunoglobulin antibody.

10. The method of claim 6 wherein the unlabeled antibody is an anti-label antibody,-the signal-emitting properties of the label not being diminished by antibody binding.

11. The method of claim 1, including partially purifying the primary antibody before labeling.

12. The method of claim 11 wherein the primary antibody is partially purified by ammonium sulfate fractionation, ion exchange chromatography, gel filtration chromatography, affinity chromatography, or a combination thereof.

13. The method of claim 1 wherein the unlabeled cross-linking agent is not completely specific for the primary antibody.

14. The method of claim 1 wherein the primary antibody is a polyclonal antibody.

15. A method of identifying and enumerating a subclass of T-lymphocytes in a heterogeneous population of cells, comprising:
    (a) contacting a sample from said heterogeneous population of cells with a primary labeled antibody which recognizes and binds to an antigenic determinant of an antigen specific for a subclass of T-lymphocytes whose identification and enumeration is desired;

(b) washing said sample to remove unbound labeled primary antibody;

(c) contacting said sample with a second, unlabeled antibody which recognizes and binds to said primary labeled antibody previously bound to the T-lymphocyte antigenic determinant within the plane of the cellular membrane;

(d) detecting the lymphocytes which have been labeled by binding to the primary antibody and second, unlabeled antibody; and (e) relating the detection of step (d) to the identification and enumeration of the subclass of T-lymphocytes;

wherein steps (a), (b) and (c) are carried out at the temperature of an ice bath and there is no incubation at 37° C. between steps (c) and (d).

16. The method of claim 15 wherein said antigen is characterized by a molecular weight of 55,000 Daltons.

* * * * *